United States Patent
Hoof et al.

(10) Patent No.: US 8,858,565 B1
(45) Date of Patent: Oct. 14, 2014

(54) INSERTER FOR SOFT TISSUE OR BONE-TO-BONE FIXATION DEVICE AND METHODS

(75) Inventors: Jordan A. Hoof, Phoenix, AZ (US);
Kevin N. Baird, Phoenix, AZ (US);
David G. Spilka, Phoenix, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 1399 days.

(21) Appl. No.: 12/437,007

(22) Filed: May 7, 2009

Related U.S. Application Data

(60) Provisional application No. 61/051,671, filed on May 8, 2008.

(51) Int. Cl.
*A61B 17/58* (2006.01)
*A61B 17/60* (2006.01)
*A61F 2/00* (2006.01)

(52) U.S. Cl.
USPC ........................................................ 606/104

(58) Field of Classification Search
USPC ...... 606/86 A, 86 B, 86 R, 104, 99, 305–310, 606/138; 81/60, 177.85; 411/348, 941.3
See application file for complete search history.

(56) References Cited

U.S. PATENT DOCUMENTS

| | | | |
|---|---|---|---|
| 3,708,883 A | 1/1973 | Flander | |
| 3,832,931 A | 9/1974 | Talan | |
| 4,311,421 A | 1/1982 | Okada et al. | |
| 4,711,232 A | 12/1987 | Fischer et al. | |
| 4,716,893 A | 1/1988 | Fischer et al. | |
| 4,738,255 A | 4/1988 | Goble et al. | |
| 4,744,793 A | 5/1988 | Parr et al. | |
| 4,772,286 A | 9/1988 | Goble et al. | |
| 4,778,468 A | 10/1988 | Hunt et al. | |
| 4,828,562 A | 5/1989 | Kenna | |
| 4,870,957 A | 10/1989 | Goble et al. | |

(Continued)

FOREIGN PATENT DOCUMENTS

| | | |
|---|---|---|
| CA | 2235354 A1 | 10/1999 |
| EP | 0232049 B1 | 3/1990 |

(Continued)

OTHER PUBLICATIONS

Caborn et al., A Biomechanical Comparison of Initial Soft Tissue Tibial Fixation Devices: The Intrafix Versus a Tapered 35-mm Bioabsorbable Interference Screw, The American Journal of Sports Medicine, 2004, vol. 32, No. 4.

(Continued)

*Primary Examiner* — Kevin Truong
*Assistant Examiner* — Sameul Hanna
(74) *Attorney, Agent, or Firm* — Donald E. Stout; Stout, Uxa & Buyan, LLP

(57) ABSTRACT

A positioning and installation tool for a fixation implant is inserted through a single, simple drill hole and positioned in place. The device controls the degree to which the implant is deployed and prevents accidental disengagement of the device from the implant before deployment has completed. The device also guides the components of the implant involved in active tendon compression at the aperture of the bone tunnel. The implant is deployed simply by rotating a knob, thereby creating an anchor point of high stiffness and fixation strength. When deployment has completed, the inserter is disengaged from the affixed implant by simply pulling a release mechanism.

19 Claims, 3 Drawing Sheets

(56) References Cited

U.S. PATENT DOCUMENTS

| | | | |
|---|---|---|---|
| 4,955,910 A | 9/1990 | Bolesky | |
| 4,957,498 A | 9/1990 | Caspari et al. | |
| 5,004,474 A | 4/1991 | Fronk et al. | |
| 5,037,422 A | 8/1991 | Hayhurst et al. | |
| 5,085,661 A | 2/1992 | Moss | |
| 5,139,520 A | 8/1992 | Rosenberg | |
| 5,161,916 A | 11/1992 | White et al. | |
| 5,176,709 A | 1/1993 | Branemark | |
| 5,188,636 A | 2/1993 | Fedotov | |
| 5,211,647 A | 5/1993 | Schmieding | |
| 5,234,430 A | 8/1993 | Huebner | |
| 5,236,445 A | 8/1993 | Hayhurst et al. | |
| 5,258,016 A | 11/1993 | DiPoto et al. | |
| 5,268,001 A | 12/1993 | Nicholson et al. | |
| 5,281,237 A | 1/1994 | Gimpelson | |
| 5,320,626 A | 6/1994 | Schmieding | |
| 5,336,240 A | 8/1994 | Metzler et al. | |
| 5,350,383 A | 9/1994 | Schmieding et al. | |
| 5,354,298 A | 10/1994 | Lee et al. | |
| 5,356,435 A | 10/1994 | Thein | |
| 5,364,398 A * | 11/1994 | Chapman et al. | 606/71 |
| 5,365,807 A * | 11/1994 | Darrah et al. | 81/60 |
| 5,374,269 A | 12/1994 | Rosenberg | |
| 5,383,878 A | 1/1995 | Roger et al. | |
| 5,411,523 A | 5/1995 | Goble | |
| 5,431,651 A | 7/1995 | Goble | |
| 5,431,666 A | 7/1995 | Sauer et al. | |
| 5,439,467 A | 8/1995 | Benderev et al. | |
| 5,456,685 A | 10/1995 | Huebner | |
| 5,464,427 A | 11/1995 | Curtis et al. | |
| 5,466,237 A | 11/1995 | Byrd et al. | |
| 5,474,555 A | 12/1995 | Puno et al. | |
| 5,478,341 A * | 12/1995 | Cook et al. | 606/62 |
| 5,480,403 A | 1/1996 | Lee et al. | |
| 5,486,197 A | 1/1996 | Le et al. | |
| 5,507,750 A | 4/1996 | Goble et al. | |
| 5,571,104 A | 11/1996 | Li | |
| 5,571,184 A | 11/1996 | DeSatnick | |
| 5,575,819 A | 11/1996 | Amis | |
| 5,578,048 A * | 11/1996 | Pasqualucci et al. | 606/192 |
| 5,598,612 A * | 2/1997 | Sheldon | 24/635 |
| 5,601,562 A | 2/1997 | Wolf et al. | |
| 5,603,716 A | 2/1997 | Morgan et al. | |
| 5,618,314 A | 4/1997 | Harwin et al. | |
| 5,632,748 A | 5/1997 | Beck, Jr. et al. | |
| 5,645,589 A | 7/1997 | Li | |
| 5,667,513 A * | 9/1997 | Torrie et al. | 606/104 |
| 5,702,215 A | 12/1997 | Li | |
| 5,702,397 A | 12/1997 | Goble et al. | |
| 5,707,395 A | 1/1998 | Li | |
| 5,713,903 A | 2/1998 | Sander et al. | |
| 5,718,706 A | 2/1998 | Roger | |
| 5,725,529 A | 3/1998 | Nicholson et al. | |
| 5,725,541 A | 3/1998 | Anspach, III et al. | |
| 5,728,136 A | 3/1998 | Thal | |
| 5,741,300 A | 4/1998 | Li | |
| 5,743,912 A | 4/1998 | Lahille et al. | |
| 5,769,894 A | 6/1998 | Ferragamo | |
| 5,782,865 A | 7/1998 | Grotz | |
| 5,814,073 A | 9/1998 | Bonutti | |
| 5,845,645 A | 12/1998 | Bonutti | |
| 5,846,254 A * | 12/1998 | Schulze et al. | 606/148 |
| 5,871,504 A | 2/1999 | Eaton et al. | |
| 5,899,938 A | 5/1999 | Sklar et al. | |
| 5,902,303 A | 5/1999 | Eckhoff et al. | |
| 5,911,721 A | 6/1999 | Nicholson et al. | |
| RE36,289 E | 8/1999 | Le et al. | |
| 5,931,869 A | 8/1999 | Boucher et al. | |
| 5,935,129 A | 8/1999 | McDevitt et al. | |
| 5,941,901 A | 8/1999 | Egan | |
| 5,957,953 A | 9/1999 | DePoto et al. | |
| 5,961,520 A | 10/1999 | Beck, Jr. et al. | |
| 5,964,764 A | 10/1999 | West, Jr. et al. | |
| 5,968,078 A | 10/1999 | Grotz | |
| 5,993,459 A | 11/1999 | Larsen et al. | |
| 6,017,346 A | 1/2000 | Grotz | |
| 6,086,608 A | 7/2000 | Ek et al. | |
| 6,099,530 A | 8/2000 | Simonian et al. | |
| 6,113,609 A | 9/2000 | Adams | |
| 6,117,173 A | 9/2000 | Taddia et al. | |
| 6,132,433 A | 10/2000 | Whelan | |
| 6,146,406 A | 11/2000 | Shiuzas et al. | |
| 6,152,928 A | 11/2000 | Wenstrom, Jr. | |
| 6,179,840 B1 | 1/2001 | Bowman | |
| 6,187,008 B1 | 2/2001 | Hamman | |
| 6,190,411 B1 | 2/2001 | Lo | |
| 6,214,007 B1 | 4/2001 | Anderson | |
| 6,221,107 B1 | 4/2001 | Steiner et al. | |
| 6,325,804 B1 | 12/2001 | Wenstrom, Jr. et al. | |
| 6,328,758 B1 | 12/2001 | Tornier et al. | |
| 6,355,066 B1 | 3/2002 | Kim | |
| 6,379,361 B1 | 4/2002 | Beck, Jr. et al. | |
| 6,387,129 B2 | 5/2002 | Rieser et al. | |
| 6,461,373 B2 | 10/2002 | Wyman et al. | |
| 6,482,210 B1 | 11/2002 | Skiba et al. | |
| 6,517,579 B1 | 2/2003 | Paulos et al. | |
| 6,533,795 B1 * | 3/2003 | Tran et al. | 606/144 |
| 6,533,816 B2 | 3/2003 | Sklar | |
| 6,551,330 B1 * | 4/2003 | Bain et al. | 606/144 |
| 6,554,862 B2 | 4/2003 | Hays et al. | |
| 6,562,071 B2 | 5/2003 | Jarvinen | |
| 6,599,295 B1 * | 7/2003 | Tornier et al. | 606/104 |
| 6,616,694 B1 | 9/2003 | Hart | |
| 6,623,524 B2 | 9/2003 | Schmieding | |
| 6,632,245 B2 | 10/2003 | Kim | |
| 6,648,890 B2 | 11/2003 | Culbert et al. | |
| 6,656,183 B2 | 12/2003 | Colleran et al. | |
| 6,685,706 B2 | 2/2004 | Padget et al. | |
| 6,716,234 B2 | 4/2004 | Grafton et al. | |
| 6,730,124 B2 | 5/2004 | Steiner | |
| 6,736,829 B1 | 5/2004 | Li et al. | |
| 6,736,847 B2 | 5/2004 | Seyr et al. | |
| 6,752,831 B2 | 6/2004 | Sybert et al. | |
| 6,770,073 B2 | 8/2004 | McDevitt et al. | |
| 6,770,084 B1 | 8/2004 | Bain et al. | |
| 6,780,188 B2 | 8/2004 | Clark et al. | |
| 6,796,977 B2 | 9/2004 | Yap et al. | |
| 6,802,862 B1 | 10/2004 | Roger et al. | |
| 6,833,005 B1 | 12/2004 | Mantas et al. | |
| 6,887,271 B2 | 5/2005 | Justin et al. | |
| 6,890,354 B2 | 5/2005 | Steiner et al. | |
| 6,932,841 B2 | 8/2005 | Sklar et al. | |
| 6,939,379 B2 | 9/2005 | Sklar | |
| 6,942,666 B2 | 9/2005 | Overaker et al. | |
| 6,942,668 B2 | 9/2005 | Padget et al. | |
| 6,986,781 B2 | 1/2006 | Smith | |
| 7,008,451 B2 | 3/2006 | Justin et al. | |
| 7,037,324 B2 | 5/2006 | Martinek | |
| 7,083,638 B2 | 8/2006 | Foerster | |
| 7,201,754 B2 | 4/2007 | Stewart et al. | |
| 7,309,355 B2 | 12/2007 | Donnelly et al. | |
| 7,326,247 B2 | 2/2008 | Schmieding et al. | |
| 7,556,629 B2 | 7/2009 | Von Hoffmann et al. | |
| 7,556,640 B2 | 7/2009 | Foerster | |
| 2002/0115999 A1 * | 8/2002 | McDevitt et al. | 606/60 |
| 2002/0120280 A1 | 8/2002 | Wotton, III | |
| 2002/0165611 A1 | 11/2002 | Enzerink et al. | |
| 2003/0065391 A1 | 4/2003 | Re et al. | |
| 2003/0083662 A1 | 5/2003 | Middleton | |
| 2003/0109900 A1 | 6/2003 | Martinek | |
| 2003/0135274 A1 | 7/2003 | Hays et al. | |
| 2003/0191478 A1 * | 10/2003 | Kortenbach et al. | 606/142 |
| 2003/0199877 A1 | 10/2003 | Steiger et al. | |
| 2003/0204204 A1 | 10/2003 | Bonutti | |
| 2004/0024456 A1 | 2/2004 | Brown, Jr. et al. | |
| 2004/0068267 A1 | 4/2004 | Harvie et al. | |
| 2004/0068269 A1 * | 4/2004 | Bonati et al. | 606/104 |
| 2004/0097943 A1 | 5/2004 | Hart | |
| 2004/0097988 A1 * | 5/2004 | Gittings et al. | 606/153 |
| 2004/0098050 A1 | 5/2004 | Foerster et al. | |
| 2004/0098052 A1 | 5/2004 | West, Jr. et al. | |
| 2004/0122435 A1 * | 6/2004 | Green et al. | 606/86 |
| 2004/0153153 A1 | 8/2004 | Elson et al. | |
| 2004/0180308 A1 | 9/2004 | Ebi et al. | |

(56) References Cited

U.S. PATENT DOCUMENTS

| | | | |
|---|---|---|---|
| 2004/0181240 | A1 | 9/2004 | Tseng et al. |
| 2004/0199165 | A1 | 10/2004 | Culbert et al. |
| 2004/0230194 | A1 | 11/2004 | Urbanski et al. |
| 2004/0237362 | A1 | 12/2004 | O'Connell |
| 2004/0267362 | A1 | 12/2004 | Hwang et al. |
| 2005/0033289 | A1 | 2/2005 | Warren et al. |
| 2005/0222576 | A1* | 10/2005 | Kick et al. .................... 606/104 |
| 2005/0251260 | A1 | 11/2005 | Gerber et al. |
| 2006/0095131 | A1 | 5/2006 | Justin et al. |
| 2006/0155287 | A1 | 7/2006 | Montgomery et al. |
| 2006/0189996 | A1* | 8/2006 | Orbay et al. .................... 606/87 |
| 2007/0214916 | A1* | 9/2007 | Lee .............................. 81/177.1 |
| 2007/0270842 | A1* | 11/2007 | Bankoski et al. ................ 606/61 |
| 2008/0119929 | A1 | 5/2008 | Schmieding et al. |
| 2008/0188897 | A1* | 8/2008 | Krebs et al. .................... 606/300 |
| 2008/0215061 | A1* | 9/2008 | Schumacher et al. ........ 606/104 |

FOREIGN PATENT DOCUMENTS

| | | |
|---|---|---|
| EP | 0528573 A1 | 8/1992 |
| EP | 0688185 A1 | 2/1993 |
| EP | 1033115 A2 | 9/2000 |
| EP | 0762850 B1 | 2/2004 |
| EP | 0739185 B1 | 9/2004 |
| EP | 1011535 B1 | 12/2005 |
| FR | 2696925 A1 | 4/1994 |
| JP | 10155820 A | 6/1998 |
| WO | 8809157 | 12/1988 |
| WO | 9216167 A1 | 10/1992 |
| WO | 9515726 A1 | 6/1995 |
| WO | 9812991 A1 | 4/1998 |
| WO | 9818409 | 5/1998 |
| WO | 0130253 A1 | 5/2001 |
| WO | 02085256 A1 | 10/2002 |

OTHER PUBLICATIONS

Charlton et al., Clinical Outcome of Anterior Cruciate Ligament Reconstruction with Quadrupled Hamstring Tendon Graft and Bioabsorbable Interference Screw Fixation, The American Journal of Sports Medicine, 2003, pp. 518-521, vol. 31, No. 4, Kerlan-Jobe Orthopaedic Clinic, Los Angeles.

Morgan et al., Anatomic Graft Fixation Using a Retrograde Biointerference Screw for Endoscopic Anterior Cruciate Ligament Reconstruction: Single-Bundle and 2-Bundle Techniques, Techniques in Orthopaedics, 2005, pp. 297-302, vol. 20, No. 3, Lippincott Williams & Wilkins, Inc., Philadelphia.

Robbe et al., Graft Fixation Alternatives in Anterior Cruciate Ligament Reconstruction, Spring 2002, pp. 21-28, vol. 15, Orthopaedic Surgery Department, University of Kentucky School of Medicine, Lexington, KY, U.S.A.

Scheffler et al., Biomechanical Comparison of Hamstring and Patellar Tendon Graft Anterior Cruciate Ligament Reconstruction Techniques: The Impact of Fixation Level and Fixation Method Under Cyclic Loading, Arthroscopy: The Journal of Arthroscopic and Related Surgery, Mar. 2002, pp. 304-315, vol. 18, No. 3, Arthroscopy Association of North America.

Simonian et al., Interference Screw Position and Hamstring Graft Location for Anterior Cruciate Ligament Reconstruction, The Journal of Arthroscopic and Related Surgery, Jul.-Aug. 1998, pp. 459-464, vol. 14, No. 5, The New York Hospital-Cornell University Medical College, New York, U.S.A.

Wolf, Eugene M., Hamstring Anterior Cruciate Ligament, Reconstruction using Femoral Cross-pin Fixation, Operative Techniques in Sports Medicine, Oct. 1999, pp. 241-222, vol. 7, No. 4, W.B. Saunders Company, San Francisco, U.S.A.

A Biomechanical Comparison of Femoral RetroScrew Placement in a Porcine Model, Arthrex Research and Development, 2007, Arthex, Inc.

Scope This Out: A Technical Pearls Newsletter for Arthroscopists, Fall 1999, vol. 1, No. 3, Arthrex, Inc, U.S.A.

Scope This Out: A Technical Pearls Newsletter for Arthroscopists, Summer 2001, vol. 3, No. 2, Arthrex, Inc, U.S.A.

Scope This Out: A Technical Pearls Newsletter for Arthroscopists, Summer 2002, vol. 4, No. 2, Arthrex, Inc, U.S.A.

Scope This Out: A Technical Pearls Newsletter for Arthroscopists, Summer 2002, vol. 5, No. 2, Arthrex, Inc, U.S.A.

* cited by examiner

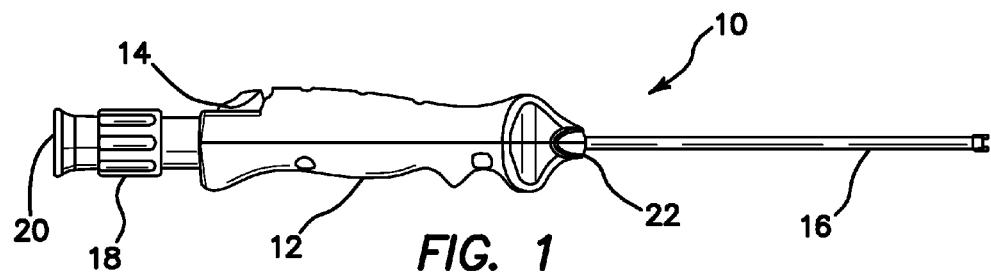
FIG. 1
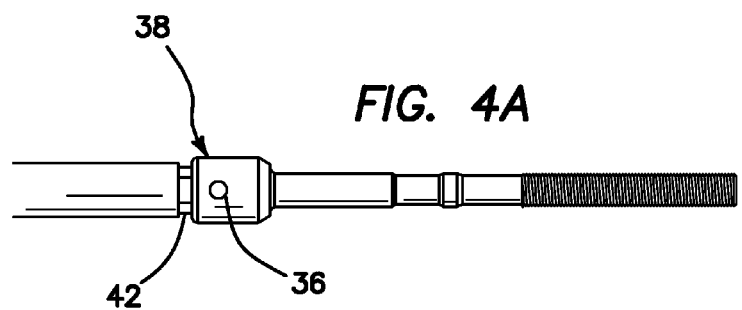
FIG. 4A
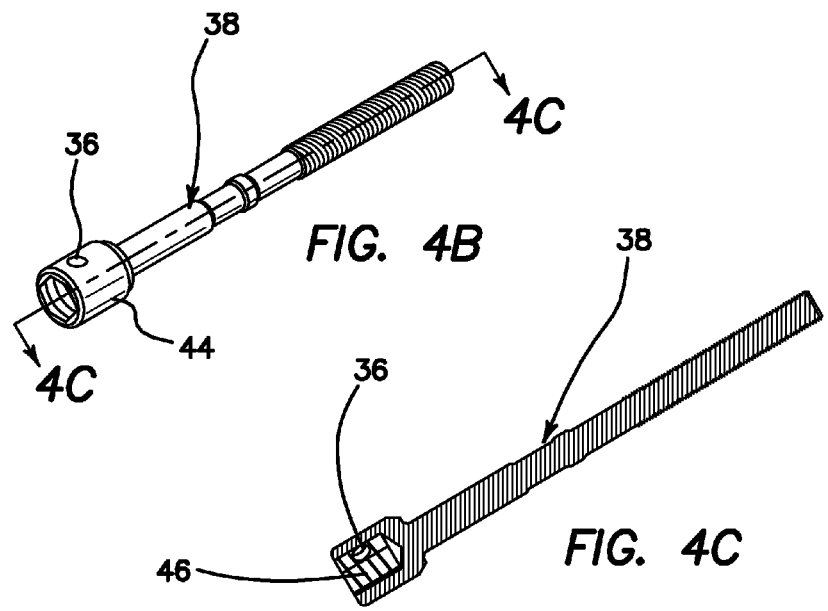
FIG. 4B
FIG. 4C

INSERTER FOR SOFT TISSUE OR BONE-TO-BONE FIXATION DEVICE AND METHODS

CROSS-REFERENCE TO RELATED APPLICATIONS

This application claims the benefit under 35 U.S.C. 119(e) of the filing date of Provisional U.S. Application Ser. No. 61/051,671, entitled Inserter for Soft Tissue or Bone-to-Bone Fixation Device, filed on May 8, 2009, which application is expressly incorporated herein by reference, in its entirety.

BACKGROUND OF THE INVENTION

The present invention relates generally to devices, systems and methods for material fixation, and, more particularly, to insertion devices for fixation implants utilized to attach soft tissue to bone, for the purpose of the repair of many soft tissue injuries, such as in the reconstruction of the Anterior Cruciate Ligament (ACL).

SUMMARY OF THE INVENTION

The disclosed invention is an inserter, intended to be used in conjunction with a soft tissue or bone-to-bone fixation device that will allow a surgeon to repair many soft tissue injuries, such as an Anterior Cruciate Ligament (ACL) injury. The bone-to-bone fixation device, once loaded with a soft tissue graft, is deployed into a prepared bone tunnel using the invention described herein. The fixation implant is packaged sterile and preloaded onto the inserter. In a preferred embodiment, the disclosed inserter device may be utilized with a fixation implant of the type disclosed in commonly assigned U.S. patent application Ser. No. 11/923,526 (the '526 application), entitled Methods and Systems for Material Fixation, filed on Oct. 24, 2007, and herein expressly incorporated by reference in its entirety.

Current ACL repairs may be difficult to perform, require more steps, additional procedure time, extra drilling, external jigs or fixtures or multiple assistants. The device is an easy to use positioning and installation tool for a femoral implant of the type disclosed in the '526 application. The device is inserted through a single, simple drill hole and positioned into place. The device controls the degree to which the implant is deployed and prevents accidental disengagement from the implant before deployment has completed. The device also guides the components of the implant involved in active tendon compression at the aperture of the femoral tunnel. The implant is deployed simply by rotating a knob, thereby creating a femoral anchor point of high stiffness and fixation strength. When deployment has completed, the inserter is disengaged from the affixed implant by simply pulling a release mechanism.

The use of the device is straightforward, eliminating potential for confusion that may arise when using other femoral fixation technologies. No additional accessories or steps are required. The only required step in preparation for fixation is to locate and drill a single tunnel within the femur. The device is designed to be used by a single operator to minimize the time and cost required to perform the procedure.

More particularly, there is provided a device for positioning and deploying a fixation implant, which comprises a handle, an insertion shaft extending distally from the handle, an implant retention mechanism disposed on a distal end of the insertion shaft, an implant deployment control disposed on the handle, and an implant release control disposed on the handle. A suture cleat is also preferably disposed on the handle, on which suture may be wrapped. A safety mechanism is disposed on the device for preventing unintentional actuation of the deployment control. Preferably, the deployment control comprises a rotatable knob and the safety mechanism comprises a safety pin which is removable to permit rotation of the rotatable deployment knob.

The inventive insertion device further comprises a mechanism for limiting rotation of the deployment knob to only one direction, wherein because the deployment knob may only be rotated in one direction, the deployment knob may be advanced distally, but not retracted proximally. The implant retention mechanism comprises a ball detent mechanism. The ball detent mechanism comprises a detent ball, a detent ball retainer, and a ball detent rod. An insertion shaft spring is disposed on the ball detent rod.

The fixation implant comprises an implant screw for deploying the fixation implant. The implant screw comprises a head having a hole for engaging the detent ball. The implant release control comprises a knob which is movable proximally to disengage the implant retention mechanism from a fixation implant engaged therewith. A hex tube is disposed at the distal end of the insertion shaft. The implant retention mechanism is disposed on the hex tube and the hex tube has a recess for receiving a portion of the fixation implant.

The implant screw further comprises internal left-hand threads disposed on an interior surface in the head, defining the hole, so that the implant screw may be disengaged from the fixation implant. A shaft having external threads extends distally from the implant screw head.

In another aspect of the invention, there is provided a fixation implant for securing soft tissue to bone or bone to bone, wherein the fixation implant comprises an implant screw for deploying the fixation implant. The implant screw comprises a head having a hole for engaging a detent ball forming part of an implant retention mechanism on an insertion tool. The implant screw further comprises internal left-hand threads disposed on an interior surface in the head, defining said hole, so that the implant screw may be disengaged from the fixation implant, and a shaft having external threads, extending distally from the head.

In still another aspect of the invention, there is disclosed a method for inserting a deployable fixation implant into an opening in bone. This method comprises steps of retaining the fixation implant on a distal end of an insertion tool, positioning the insertion tool in a desired bone opening, disengaging a safety mechanism so that a deployment control on the insertion tool may be actuated to deploy the fixation implant, and actuating the deployment control to advance of component of the fixation implant distally, so that portions of the fixation implant are expanded radially to engage adjacent bone. The disengaging step comprises removing a safety pin from the insertion tool to thereby permit rotation of the deployment control, and the actuation step comprises rotating a knob of the deployment control. The inventive method further comprises a step of releasing the fixation implant from the insertion tool.

The invention, together with additional features and advantages thereof, may best be understood by reference to the following description taken in conjunction with the accompanying illustrative drawing.

BRIEF DESCRIPTION OF THE DRAWINGS

FIG. 1 is a plan view of an insertion device constructed in accordance with the principles of the present invention;

FIG. 4A is a plan view of an implant screw which forms a part of the implant being deployed, utilized on conjunction with the insertion device of FIGS. 1-3 for deploying an implant;

FIG. 4B is a perspective view of the implant screw shown in FIG. 4A; and

FIG. 4C is a cross-sectional view of the implant screw of FIG. 4B, taken along line 4C-4C.

DESCRIPTION OF THE PREFERRED EMBODIMENT

Figure 2:
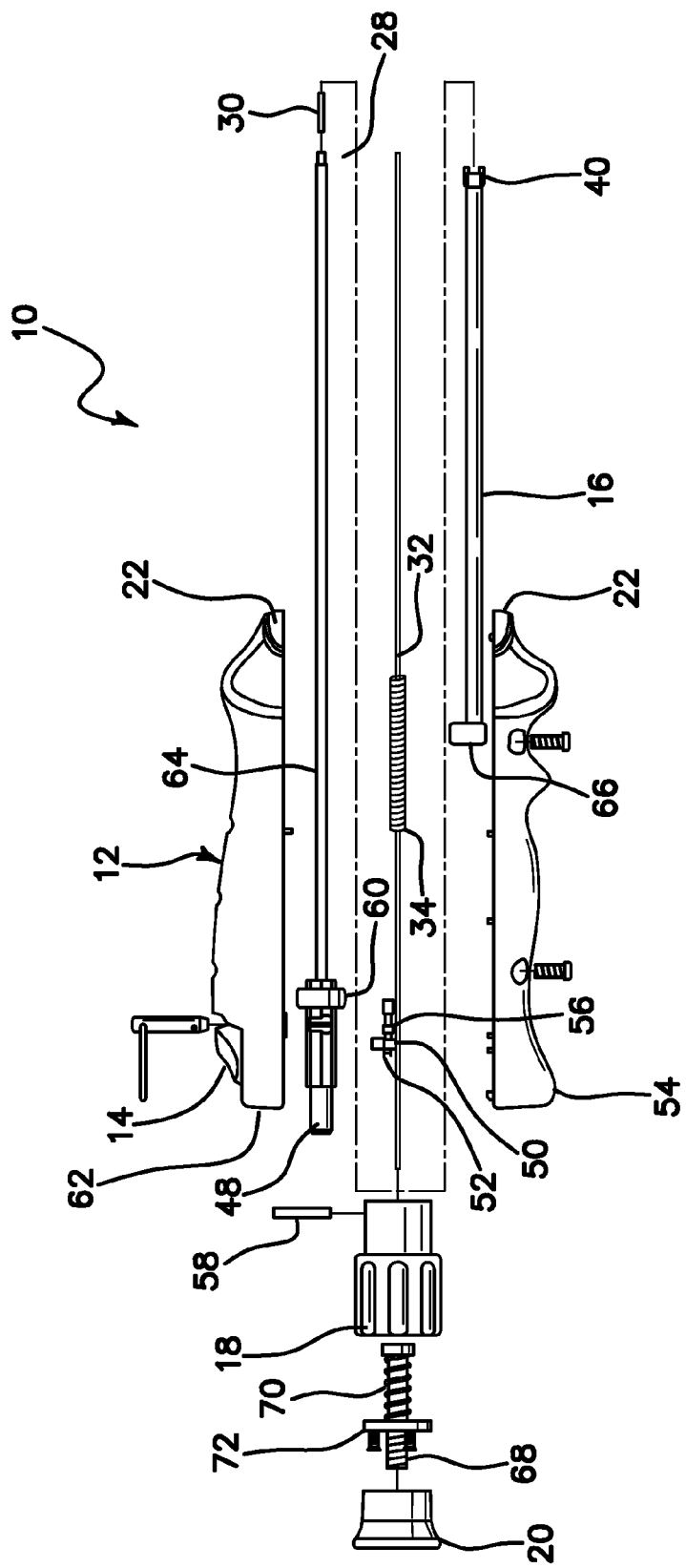
FIG. 2 is an exploded view of the insertion device illustrated in FIG. 1.

The device 10 of the present invention is an inserter, used for positioning and deployment of a fixation implant like that described in the '526 application. The user interface features of the inserter 10, depicted in FIG. 1, are a handle 12, a safety pin 14, an insertion shaft 16, a deployment knob 18, a release knob 20, and suture cleats 22.

At the end of the insertion device 10, a sutured soft tissue graft (not shown) is loaded onto the implant (not shown), and the free suture strands (not shown) are secured to the suture cleats 22 to allow for suture management and easy insertion of the graft complex. The suture cleats 22 are designed to be easily and quickly wrapped with suture. After the suture has been attached to the cleats, the inserter is placed inside a femoral tunnel 24 in the femur 26 of a patient (FIG. 3). When it has reached the desired deployment location, the inserter and implant are deployed. Deployment is performed by removing the safety pin 14 and rotating the deployment knob 18 in a clockwise fashion until the deployment knob 18 comes into contact with the inserter handle 12, or until it can no longer be turned. An implant (not shown) is attached to the tip of the insertion shaft 16 by means of a ball detent mechanism (FIG. 2), comprising a detent ball 28, a detent ball retainer 30, and a ball detent rod 32, on which is disposed an insertion shaft spring 34. The ball detent mechanism engages with a hole 36 (FIG. 4A, 4B, 4C) in an implant screw 38. Deployment motion of the inserter 10 is ratcheted and is limited to the clockwise direction to prevent accidental undeployment. By rotating the deployment knob 18, the diamond wedge of the implant expands the implant arms outward, which provide fixation by engaging against the wall of the femoral tunnel 24. To disengage the implant from the inserter 10, the implant release knob 20 is pulled, releasing the detent mechanism. The insertion device can then be removed from the soft tissue graft implant site after any suture has been detached from the suture cleats 22.

The device may come preloaded with the fixation implant attached to the inserter tip 40 (FIG. 3). FIGS. 4A-4C show the implant screw 38, held to a hex tube 42 of the inserter 10 by means of the aforementioned ball detent mechanism and hole 36 in the implant screw. The head 44 of the implant screw 38 has internal left hand threads 46 (FIG. 4C) in order to remove the screw if a revision of the implant should be necessary. To remove the screw, a left-hand threaded removal tool is screwed into the hex head 44 of the screw, securing the screw to the removal tool. The tool is then rotated in a counterclockwise direction to unscrew and disengage the screw from the implant.

Figure 3:
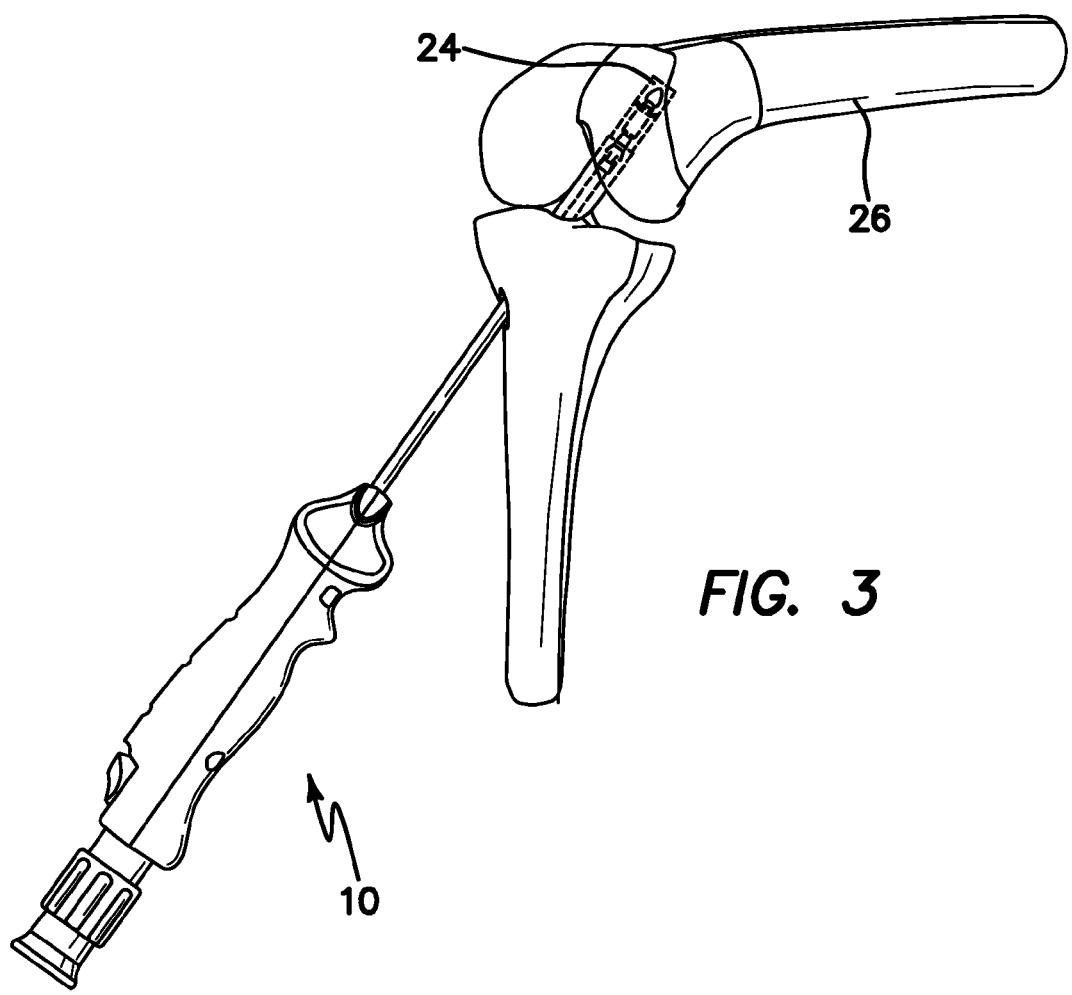
FIG. 3 is a plan view of the insertion device of FIGS. 1 and 2 as it is being utilized for deploying an implant into a bone tunnel.

Now referring more particularly to FIG. 2, a threaded ratchet shaft 48 has a multitude of cuts running parallel to its length, designed to engage a pawl 50, limiting its rotation to the clockwise direction. The pawl 50 is fitted over a pawl axle 52 which rests inside a mated cavity in a handle bottom 54. As the threaded ratchet shaft 48 rotates clockwise, the pawl 50 is deflected downwards towards the handle bottom 54. When the pawl 50 comes into contact with one of the cuts in the threaded ratchet shaft 48, it is returned to the engaging antirotation position by a torsion spring 56. If motion is attempted in the counterclockwise direction, the flat face of the cutout in the threaded ratchet shaft 48 engages the flat face of the pawl 50, preventing antirotation. A leaf spring may be substituted for the pawl 50 and torsion spring 56 if it is positioned such that it engages the flat face of the threaded ratchet shaft 48.

The deployment knob 18 may be attached to the threaded ratchet shaft 48 by means of an alignment pin 58. As the deployment knob 18 rotates the threaded ratchet shaft 48 in a clockwise direction, it is translated linearly forward by a stationary translation nut 60. The translation nut 60 is fitted inside a cavity in the handle bottom 54 and the handle top 62. The deployment tube 64, which engages with and turns the implant screw, is affixed to the threaded ratchet shaft 48. The threaded ratchet shaft 48 and implant screw are threaded so that the turn to travel ratio are 1:1 between the two components. Therefore, as the threaded ratchet shaft 48 and deployment tube 64 rotate, the per-turn linear travel of the threaded ratchet shaft 48 is equal to the linear travel of the implant screw within the implant body.

The inserter tip 40 interfaces with the compression pads on the femoral implant to prevent implant rotation and assists in aligning and guiding the compression pads as they separate. The insertion shaft 16 is preferably a hollow cylindrical collar that is allowed to freely slide over the deployment tube 64. An anti-rotation washer 66 has a machined groove that aligns to a longitudinal rib in the handle top 62. The anti-rotation washer has a positive spring bias created by the insertion shaft spring 34. The insertion shaft spring 34 is constrained by a rib within the handle top 62. As the assembly of the inserter tip 40, insertion shaft 16, and anti-rotation washer 66 moves distally during the course of implant deployment, the insertion shaft spring 34 compresses, providing a reaction force that ensures the inserter tip 40 remains engaged with the implant.

The deployment tube 64 contains a hollow cylindrical center portion that allows the ball detent rod 32 to slide freely within. The ball detent rod 32 also fits within the detent ball retainer 30 that is fixed inside the tip of the deployment tube 64. The purpose of the detent ball retainer 30 is to retain the detent ball 28 within the deployment tube 64 and to constrain its motion inwards and outwards from the engaging hex face of the deployment tube 64. The inside engaging hex face of the deployment tube 64 is drilled in such a manner that the detent ball 28 is prevented from falling out of the assembly yet is still allowed to protrude enough for significant engagement with the implant screw.

The detent ball 28 is sandwiched above the detent ball retainer 30 and below the engaging hex face of the deployment tube 64. As the ball detent rod 32 slides into the detent ball retainer 30, it pushes the detent ball 28 from the engaging hex face of the deployment tube 64. In this state, the detent ball 28 protrudes a distance out of the engaging hex face of the deployment tube 64 and is prevented from retracting back into the engaging hex face by the support of the ball detent rod 32 underneath.

The ball detent rod 32 is connected to a spring shaft 68 which is equipped with an engagement spring 70 that translates a positive engagement force to the ball detent rod 32. The engagement spring 70 is confined within the deployment knob 18 and a deployment knob cover 72 which it is compressed by when the spring shaft 68 is retracted.

It is to be understood that the figures of the bone and anchors seen above are purely illustrative in nature, and are not intended to limit the application of the inventive embodiments to any particular physiological application or purpose. The invention is applicable to many different types of procedures involving, in particular, the attachment of connective or soft tissue to bone. All of the terms used herein are descriptive rather than limiting, and many changes, modifications, and substitutions may be made by one having ordinary skill in the art without departing from the spirit and scope of the invention, which is to be limited only in accordance with the following claims.

What is claimed is:

1. A device for positioning and deploying a fixation implant, comprising:
    a handle;
    an insertion shaft extending distally from said handle;
    an implant retention mechanism disposed on a distal end of said insertion shaft, wherein the implant retention mechanism is configured to engage the insertion shaft to the fixation implant;
    an implant deployment control comprising a rotatable knob disposed on said handle, wherein rotation of the knob deploys the implant retention mechanism;
    an implant release control disposed on said handle, wherein movement of the implant release control relative to the handle retracts the implant retention mechanism to release the implant retention mechanism;
    a safety mechanism disposed on said handle for preventing unintentional actuation of the deployment control, said safety mechanism comprising a safety pin which in a first position prevents rotation of the rotatable deployment knob and in a second position permits rotation of the rotatable deployment knob; and
    a deployment mechanism for limiting rotation of the deployment knob to only one direction, wherein because the deployment knob may only be rotated in one direction, the deployment mechanism may be advanced distally, but not retracted proximally.

2. The device as recited in claim 1, and further comprising a suture cleat on said handle on which suture may be wrapped.

3. The device as recited in claim 1, wherein the implant retention mechanism comprises a ball detent mechanism, said ball detent mechanism comprising a detent ball, a detent ball retainer, and a ball detent rod.

4. The device as recited in claim 3, and further comprising an insertion shaft spring disposed on said ball detent rod.

5. The device as recited in claim 3, and further comprising a fixation implant, wherein said fixation implant comprises an implant screw for deploying the fixation implant, said implant screw comprising a head having a hole for engaging said detent ball.

6. The device as recited in claim 1, wherein said implant release control comprises a knob which is movable proximally to disengage said implant retention mechanism from a fixation implant engaged therewith.

7. The device as recited in claim 1, and further comprising a hex tube disposed at the distal end of the insertion shaft, said implant retention mechanism being disposed on said hex tube, and said hex tube having a recess for receiving a portion of said fixation implant.

8. The device as recited in claim 5, wherein said implant screw further comprises internal left-hand threads disposed on an interior surface in said head, defining said hole, so that the implant screw may be disengaged from the fixation implant.

9. The device as recited in claim 8, wherein the implant screw further comprises a shaft having external threads, extending distally from said head.

10. The device as recited in claim 6, wherein said implant release knob is proximal to and coaxial with said deployment knob.

11. The device as recited in claim 6, wherein pulling said implant release knob proximally releases the implant retention mechanism.

12. The device as recited in claim 1, wherein the mechanism for limiting rotation of the deployment knob to only one direction comprises a ratchet shaft to which the deployment knob is attached.

13. The device as recited in claim 12, and further comprising a pawl for engaging the ratchet shaft, wherein engagement of the pawl with portions of the ratchet shaft operates to limit rotation of the deployment knob to only one direction.

14. A device for positioning and deploying a fixation implant, comprising:
    a handle;
    an insertion shaft extending distally from said handle;
    an implant retention mechanism disposed on a distal end of said insertion shaft, wherein the implant retention mechanism comprises a ball detent mechanism, said ball detent mechanism comprising a detent ball, a detent ball retainer, and a ball detent rod, wherein the implant retention mechanism is configured to engage the insertion shaft to the fixation implant;
    an implant deployment control comprising a rotatable knob disposed on said handle, wherein rotation of the knob deploys the implant retention mechanism;
    an implant release control disposed on said handle, wherein movement of the implant release control relative to the handle retracts the implant retention mechanism to release the implant retention mechanism;
    a safety mechanism disposed on said handle for preventing unintentional actuation of the deployment control, said safety mechanism comprising a safety pin which is removable to permit rotation of the rotatable deployment knob; and
    a fixation implant, wherein said fixation implant comprises an implant screw for deploying the fixation implant, said implant screw comprising a head having a hole for engaging said detent ball.

15. The device as recited in claim 14, and further comprising an insertion shaft spring disposed on said ball detent rod.

16. The device as recited in claim 14, wherein said implant screw further comprises internal left-hand threads disposed on an interior surface in said head, defining said hole, so that the implant screw may be disengaged from the fixation implant.

17. The device as recited in claim 16, wherein the implant screw further comprises a shaft having external threads, extending distally from said head.

18. The device as recited in claim 14, wherein said implant release knob is proximal to and coaxial with said deployment knob.

19. The device as recited in claim 14, wherein pulling said implant release knob proximally releases the implant retention mechanism.

\* \* \* \* \*